(12) United States Patent
Luginsland et al.

(10) Patent No.: US 6,380,411 B1
(45) Date of Patent: Apr. 30, 2002

(54) ORGANOSILICON COMPOUND, A PROCESS FOR ITS PREPARATION AND ITS USE

(75) Inventors: Hans-Detlef Luginsland, Köln; Christoph Batz-Sohn, Hanau; Jörg Münzenberg, Hanau; Gerd Rainhard Zezulka, Hanau, all of (DE)

(73) Assignee: Degussa-Huls AG, Frankfurt am Main (DE)

( * ) Notice: Subject to any disclaimer, the term of this patent is extended or adjusted under 35 U.S.C. 154(b) by 0 days.

(21) Appl. No.: 09/692,515

(22) Filed: Oct. 20, 2000

(30) Foreign Application Priority Data

Oct. 21, 1999 (DE) .......................... 199 50 608

(51) Int. Cl.$^7$ .................................. C07F 3/06
(52) U.S. Cl. ............... 556/9; 556/12; 524/502; 524/515; 526/335; 526/338; 526/339; 526/340
(58) Field of Search ............ 556/9, 12; 526/335, 526/338, 339, 340; 524/502, 515

(56) References Cited

U.S. PATENT DOCUMENTS

| | | | |
|---|---|---|---|
| 3,842,111 A | 10/1974 | Meyer-Simon et al. | |
| 5,107,009 A | 4/1992 | Rauleder et al. | |
| 5,196,462 A | 3/1993 | Berta | |
| 5,912,374 A | * 6/1999 | Agostini et al. | ................ 556/9 |

FOREIGN PATENT DOCUMENTS

| | | |
|---|---|---|
| DE | 2 141 159 | 3/1973 |
| DE | 40 25 866 | 2/1992 |
| EP | 0 513 699 | 5/1992 |

OTHER PUBLICATIONS

Gradwell et al., "Sulfur Vulcanization of Polyisoprene Accelerated by Benzothiazole Derivatives. II. Reaction of 2–Mercaptobenzothiazole and its Zinc Salt with Sulfur and ZnO in Polyisoprene", Journal of Applied Polymer Science, 1995, vol. 58, pp. 2193–2200.

Elias et al., Makromoleküle, Hüthig und Wepf Verlag, Heidelberg, 1992, vol. 2, pp. 484–487.

English language abstract of KR above; Derwent Acc. No. 1973–13364U/197310, 1973.

English language abstract of LR above; Derwent Acc. No. 1992–058276/199208, 1992.

English language abstract of MR above; Derwent Acc. No. 1992–383612/199247, 1992.

English language translation of VR above, 1992.

* cited by examiner

Primary Examiner—Paul F. Shaver
(74) Attorney, Agent, or Firm—Pillsbury Winthrop LLP

(57) ABSTRACT

Organosilicon compounds of general formula (I)

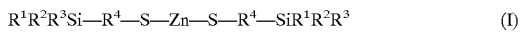

wherein $R^1$, $R^2$, R independently, represent H, a halogen, alkyl or alkoxy and $R^4$ represents an alkylidene group, their preparation and their use in rubber mixtures.

12 Claims, 1 Drawing Sheet

ORGANOSILICON COMPOUND, A PROCESS FOR ITS PREPARATION AND ITS USE

CROSS-REFERENCE TO RELATED APPLICATION

This application is based on German Application DE 199 50 608.6, filed Oct. 21, 1999, which disclosure is incorporated herein by reference.

FIELD OF THE INVENTION

The present invention provides an organosilicon compound, a process for its preparation and its use.

BACKGROUND OF THE INVENTION

It is known that sulfur-containing organosilicon compounds such as 3-mercaptopropyltrimethoxysilane, 3-mercapto-propyltriethoxysilane, 3-thiocyanatopropyltriethoxysilane or bis-(3-[triethoxysilyl]-propyl)tetrasulfane are used as silane bonding agents or reinforcing additives in oxidically filled rubber mixtures. The rubber mixtures are used, inter alia, for industrial rubber items and for parts of rubber tires, in particular for treads (DE 2 141 159, DE 2 212 239, U.S. Pat. Nos. 3,978,103, 4,048,206).

It is also known that the alkoxysilyl function, generally a trimethoxysilyl or triethoxysilyl group, reacts with silanol groups on the fillers, generally silica, during mixing-preparation and thus the silane becomes fixed onto the surface of the filler. Production of the filler/rubber bond then takes place during the vulcanization process, via the sulfur groupings on the fixed silane. Accordingly, the resulting properties of this type of vulcanizate, for a given constant amount of silane, depends critically on how high the coupling yield of the silane is and what network structure is produced. Furthermore, it is known that silanes with polysulfane functions such as, for example, bis-(3-[triethoxysilyl]-propyl)tetrasulfane, tend to participate in disadvantageous premature cross-linking during the mixing process, at appropriately high temperatures. Therefore, it is important that a maximum batch temperature of about 155° C. is not exceeded when using these silanes.

SUMMARY OF THE INVENTION

The object of the present invention is to provide organosilicon compounds which have higher coupling yields, improved rubber properties and higher process reliability than the silanes known hitherto, when used as a bonding agent or reinforcing additive in rubber mixtures.

The invention provides an organosilicon compound of the general formula I

  (I)

wherein $R^1$, $R^2$, $R^3$, independently, represent H, a halogen, a straight-chain or branched alkyl group or a straight-chain or branched alkoxy group and $R^4$ represents a straight-chain or branched alkylidene group.

The straight-chain alkyl groups may be methyl, ethyl, n-propyl, n-butyl-, n-pentyl- or n-hexyl groups. The branched alkyl groups may be iso-propyl, iso-butyl or tert-butyl groups. The halogen may be fluorine, chlorine, bromine or iodine. The alkoxy groups may be methoxy, ethoxy, propoxy, butoxy, isopropoxy, isobutoxy or pentoxy groups.

In the organosilicon compound in accordance with formula I, $R^1$, $R^2$, $R^3$ preferably represent ethoxy and $R^4$ preferably represents $CH_2CH_2CH_2$ or isobutylidene.

The invention also provides a process for preparing the organosilicon compound of the general formula (I), characterised in that a mercaptan compound of the general formula (II)

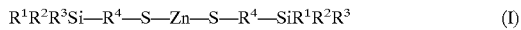  (II)

wherein $R^1$, $R^2$, $R^3$, independently, represent H, a halogen, a straight-chain or branched alkyl group or a straight-chain or branched alkoxy group and $R^4$ represents a straight-chain or branched alkylidene group, is reacted with a zinc alcoholate. The reaction may be performed in alcoholic solution. The reaction may be performed at a temperature range of 20° to 200° C., preferably 50° to 80° C.

Zinc ethanolate may be used as the zinc alcoholate. Ethanol may be used to prepare the alcoholic solution. The zinc alcoholate may be prepared by reacting zinc chloride with sodium ethanolate in alcoholic solution. The zinc alcoholate may be reacted with double the molar amount of the mercaptan compound of formula (II) in alcoholic solution.

3-Mercaptopropyltriethoxysilane may be used as a mercaptan compound. In one embodiment, a compound of formula (II) with $R^1$, $R^2$, $R^3$=ethoxy and $R^4$=$CH_2CH_2CH_2$, may be reacted with zinc ethanolate in ethanolic solution.

The organosilicon compound according to the invention is highly reactive and may be used in rubber mixtures.

Rubber mixtures which contain the organosilicon compound according to the invention as a bonding agent or as a reinforcing additive and the molded items which are produced after a vulcanization step, in particular pneumatic tires or tire treads, have a low rolling resistance with, simultaneously, good wet adhesion and high resistance to abrasion.

The invention also provides rubber mixtures, characterised in that they contain rubber, fillers, preferably precipitated silica, at least one organosilicon compound of formula (I) and optionally other rubber auxiliary substances.

The organosilicon compound of the formula (I) may be used in amounts of 0.1 to 15 wt. %, preferably 5–10 wt. %, with respect to the amount of filler used.

Natural rubber and/or synthetic rubber may be used as the rubber. Preferred synthetic rubbers are described, for example, in W. Hofmann, Kautschuktechnologie, Genter Verlag, Stuttgart 1980. The rubbers may be used individually or in combination. Anionic polymerized S-SBR rubbers with a glass transition temperature above −50° C. and its mixtures with high-cis diene rubbers are used in particular for preparing motor vehicle tires.

The following may be used as fillers:

carbon blacks, which are prepared by the lamp black, furnace black or channel black process and have a BET surface area of 20 to 200 $m^2/g$, highly disperse silicas prepared, for example, by precipitation from silicate solutions or by flame hydrolysis from silicon halides, with specific surface areas of 5 to 1000 $m^2/g$, preferably 20 to 400 $m^2/g$ (BET surface area) and with primary particle sizes of 10 to 400 nm, optionally also as mixed oxides with metal oxides such as Al, Mg, Ca, Ba, Zn and titanium oxides, synthetic silicates such as aluminum silicate, alkaline earth silicates such as, for example, magnesium silicate or calcium silicate, with BET surface areas of 20 to 400 m²/g and primary particle diameters of 10 to 400 nm, natural silicates such as kaolin and other naturally occurring silicas, glass fibers and glass fiber products (mats, ropes) or glass microbeads.

The rubber mixtures may contain synthetic rubber and silica as a filler. Highly disperse silicas, prepared by precipitation from silicate solutions, with BET surface areas of 20 to 400 m²/g are preferably used, in amounts of 10 to 150 parts by weight, with respect to 100 parts by weight of rubber.

The fillers mentioned may be used individually or as a mixture.

In a particularly preferred embodiment of the rubber mixture, 10 to 150 parts by weight of a pale filler, optionally together with 0 to 100 parts by weight of carbon black, with respect to 100 parts by weight of rubber, and 0.1 to 15 parts by weight, preferably 5 to 10 parts by weight of a compound of formula (I), with respect to 100 parts by weight of the filler used, may be used to prepare the mixtures.

The organosilicon compounds according to the invention may be used either in the pure form or attached to an inert organic or inorganic support. Preferred support materials may be silica, natural or synthetic silicates, aluminum oxide or carbon black. The organosilicon compound according to the invention may be used on its own or combined with other organosilicon compounds, in particular monofunctional alkylalkoxysilanes.

Rubber auxiliary products which may be used are reaction accelerators, reaction delayers, antioxidants, stabilizers, processing aids, plasticizers, waxes, metal oxides and activators such as triethanolamine, polyethylene glycol or hexanetriol which are well-known in the rubber industry.

The rubber auxiliary substances may be used in conventional amounts which are governed, inter alia, by the ultimate application. Conventional amounts may be 0.1 to 50 wt. %, with respect to rubber. The organosilicon compounds may be activated by adding sulfur and accelerators before the actual cross-linking reaction. This activation may take place during the vulcanization step. Suitable vulcanization accelerators may be mercaptobenzthiazoles, sulfenamides, guanidines, thiurams, dithiocarbamates, thioureas and thiocarbonates. The vulcanization accelerator and sulfur or peroxides may be used in amounts of 0.1 to 10 wt. %, preferably 0.1 to 5 wt. %, with respect to rubber.

Use of organosilicon compounds according to the invention in rubber mixtures results in advantages in the static and dynamic vulcanizate data as compared with mixtures according to the prior art. This is shown in particular by a higher tensile strength, a higher 300% stress modulus, and an improved 300%/100% stress modulus reinforcing ratio. In addition, mixtures according to the invention exhibit a decreased build-up of heat (Goodrich flexometer test), which indicates a positive hysteresis behavior, and an advantageously low loss factor tan $\delta(60°$ C.), which correlates with the rolling resistance value.

The invention also provides a process for preparing rubber mixtures, characterized in that rubber is mixed with fillers, at least one organosilicon compound of formula (I) and optionally other rubber auxiliary substances.

The organosilicon compounds according to the invention and the fillers may preferably be incorporated at bulk temperatures of 100° to 200° C., but may also be incorporated later at lower temperatures 40° to 100° C., for example together with other rubber auxiliary substances. Mixing the constituents may be performed in conventional mixing equipment such as rollers, internal mixers and mixer extruders.

Vulcanization of rubber mixtures according to the invention may take place at temperatures of 100° to 200° C., preferably 130° to 180° C., and optionally under a pressure of 10 to 200 bar. Rubber vulcanizates according to the invention may be used for molded items, for example pneumatic tires, tire treads, cable sheathing, hoses, drive belts, conveyer belts, roller coverings, tires, soles of shoes, sealing rings and damping elements.

The use of organosilicon compounds according to the invention as bonding agents or reinforcing additives in rubber mixtures leads to much higher coupling yields, and a correspondingly improved set of rubber properties, than known silanes. Organosilicon compounds according to the invention do not exhibit the known tendency to premature cross-linking of the unaccelerated mixture at high mixing temperatures. Thus, much higher processing temperatures can be tolerated with greater process reliability. Activation of the sulfur-functional group can take place only during vulcanization with the addition of sulfur and accelerator.

BRIEF DESCRIPTION OF THE DRAWING

The FIGURE shows, graphically, the torque with respect to time for an example of the invention (Ex. 5) and comparative examples (Ex. 2–4).

DETAILED DESCRIPTION OF THE PREFERRED EMBODIMENTS

EXAMPLES

Figure 1:
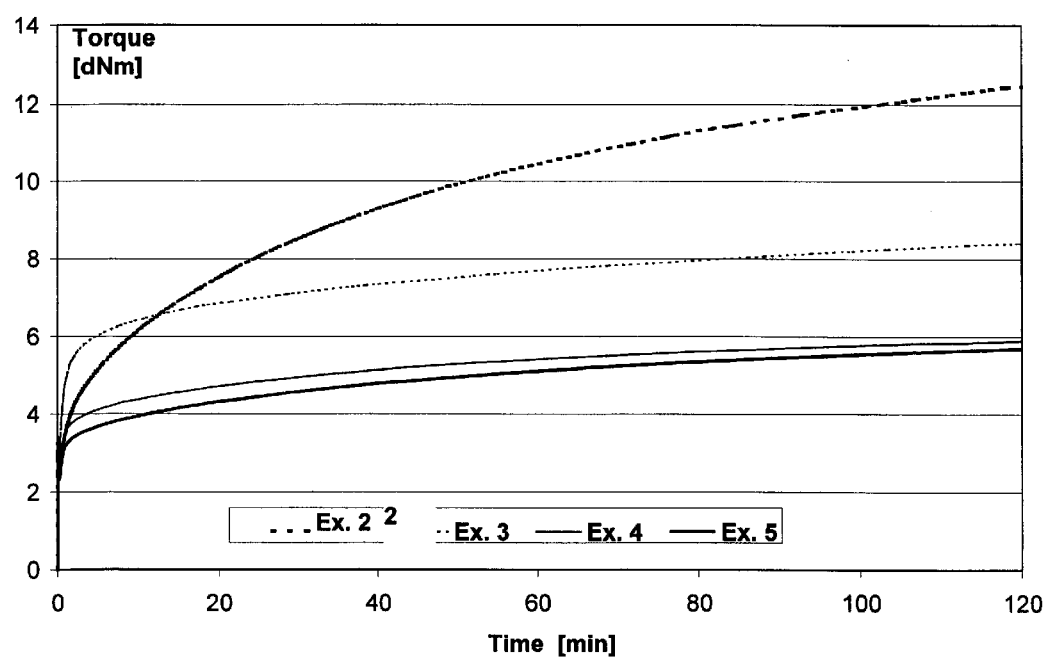

Example 1
Preparing the Zinc Organosilicon Compound

Example 1 describes preparation of an organosilicon compound in accordance with the invention.

To prepare a sodium ethanolate solution, 750 ml of ethanol is initially introduced into a 1 l flask under an atmosphere of argon and then pieces of sodium (46 g, 2 mol) are added in portions.

To prepare the zinc organosilicon compound, 750 ml of ethanol and 136.3 g (1 mol) of zinc chloride are initially introduced into a 4 l four-necked flask with a stirrer, condenser, thermometer and dropping funnel. The freshly prepared sodium ethanolate solution is then transferred to the dropping funnel and added dropwise over a period of 1 hour with stirring and heating to 78° C. The mixture is allowed to stand overnight in order to complete post-reaction and then 446.8 g (2 mol) of 3-mercaptopropyl-triethoxysilane are added dropwise over the course of 2 hours with heating. Stirring is continued for a further 4 hours at 78° C. and the mixture is then cooled to room temperature, the suspension is filtered and washed 3 times with 100 ml of ethanol. The filtrate is evaporated down to dryness and the remaining solid is dried under vacuum at 120° C. and then milled.

514.8 g of solid product are obtained, which corresponds to 95.5% of theoretical.

| Elemental analysis: | C: 38.66%, calc. 40.02% |
| --- | --- |
| | H: 7.64%, calc. 7.84% |
| | S: 11.92%, calc. 11.87% |
| | Cl: <0.1%, |

Examples 2–5
Preparing the Rubber Mixtures and Vulcanizates

In Examples 2 to 5, the preparation of rubber mixtures and vulcanizates is described. On the basis of Example 5, which contains the organosilicon compound according to the invention from Example 1 as bonding agent, the superior properties of compounds according to the invention, as compared with the prior art (Examples 2 to 4) are clear.

General Methods Used

The formulation used for the rubber mixtures is given in Table 1 below. The units phr represent the proportion by weight with respect to 100 parts of crude rubber used.

TABLE 1

| Substance | Amount [phr] |
|---|---|
| 1st stage | |
| Buna VSL 5025-1 | 96.0 |
| Buna CB 24 | 30.0 |
| Ultrasil 7000 GR | 80.0 |
| ZnO | 3.0 |
| Stearic acid | 2.0 |
| Naftolen ZD | 10.0 |
| Vulkanox 4020 | 1.5 |
| Protector G35P | 1.0 |
| Silane | as stated in the example |
| 2nd stage | |
| Batch from stage 1 | |
| 3rd stage | |
| Batch from stage 2 | |
| Vulkacit D | 2.0 |
| Vulkacit CZ | 1.5 |
| Sulfur | as stated in the example |

The polymer VSL 5025-1 is a SBR copolymer from Bayer AG, polymerized in solution, with a stirene content of 25 wt. % and a butadiene content of 75 wt. %. 73% of the butadiene is 1,2 linked, 10% is cis-1,4 and 17% is trans-1,4 linked. The copolymer contains 37.5 phr of oil and has a Mooney viscosity (ML 1+4/100° C.) of about 50.

The polymer Buna CB 24 is a cis-1,4-polybutadiene (Neodyme type) from Bayer AG, with a cis-1,4 content of 97%, a trans-1,4 content of 2%, a 1,2 content of 1% and a Mooney viscosity between 44 and 50 ME.

Ultrasil 7000 GR is a readily dispersible silica from Degussa-Hüls AG and has a BET surface area of 175 m$^2$/g.

The silane with the tradename Si 69 is bis-(3-[triethoxysilyl]-propyl)tetrasulfane, the silane Si 264 is 3-thiocyanatopropyltriethoxysilane and Dynasilan 3201 is 3-mercaptopropyltriethoxysilane. The silanes mentioned above are sold by Degussa-Hüls AG.

Naftolen ZD from Chemetall is used as an aromatic oil, Vulkanox 4020 is PPD from Bayer AG and Protector G35P is an anti-ozonant wax from HB-Fuller GmbH. Vulkacit D (DPG) and Vulkacit CZ (CBS) are commercial products from Bayer AG.

The rubber mixture is prepared in three stages, using an internal mixer, in accordance with Table 2.

TABLE 2

| Stage 1 | |
|---|---|
| Settings | |
| Mixing unit | Werner & Pfleiderer |
| Friction | 1:1.11 |
| Speed | 70 min$^{-1}$ |
| Internal pressure | 5.5 bar |
| Empty volume | 1.61 |
| Extent filled | 0.55 |
| Flow-through temp. | 70° C. |

TABLE 2-continued

| Mixing process | |
|---|---|
| 0 to 1 min | Buna VSL 5025-1 + Buna CB 24 |
| 1 to 3 min | ½ Ultrasil 7000 GR, ZnO, Stearic acid, Naftolen ZD, silane |
| 3 to 4 min | ½ Ultrasil 7000 GR, Vulkanox 4020, Protector G35P |
| 4 min | clean |
| 4 to 5 min | mix |
| 5 min | clean |
| 5 to 6 min | mix and discharge |
| Batch temp. | 140°–150° C. |
| Storage | 24 h at room temperature |

| Stage 2 | |
|---|---|
| Settings | |
| Mixing unit | same as stage 1 except: |
| Speed | 80 min$^{-1}$ |
| Extent filled | 0.53 |
| Flow-thru temp. | 80° C. |
| Mixing process | |
| 0 to 2 min | Break up batch from stage 1 |
| 2 to 5 min | Batch temperature 150° C. maintained by varying the speed |
| 5 min | Discharge |
| Batch temp. | 150°–155° C. |
| Storage | 4 h at room temperature |

| Stage 3 | |
|---|---|
| Settings | |
| Mixing unit | same as in stage 1 except: |
| Speed | 40 min$^{-1}$ |
| Extent filled | 0.51 |
| Flow-thru temp. | 50° C. |
| Mixing process | |
| 0 to 2 min | Batch from stage 2 + Vulkacit CZ + Vulkazit D + sulfur |
| 2 min | discharge and form a sheet on a laboratory mixing roller unit (diameter 200 mm, length 450 mm, flow-through temperature 50° C.) Homogenize: 3* to the left, 3* to the right cut into and fold over and also pass through 8* with a narrow roller gap (1 mm) and 3* with a wide roller gap (3.5 mm) and then draw out into a sheet |
| Batch temp. | 90°–100° C. |

The general method for preparing rubber mixtures and their vulcanizates is described in "Rubber Technology Handbook", W. Hofmann, Hanser Verlag 1994.

Rubber engineering tests were performed in accordance with the test methods described in Table 3.

TABLE 3

| Physical tests | Standard/ Conditions |
|---|---|
| ML 1 + 4, 100° C. (3rd stage) | DIN 53523/3, ISO 667 |
| Vulcameter test, 165° C. | DIN 53529/3, ISO 6502 |
| Tensile test on a ring, 23° C. | DIN 53504, ISO 37 |
| Tensile strength | |
| Modulus | |
| Extension at break | |
| Shore-A hardness, 23° C. | DIN 53 505 |
| Ball rebound, 23° C. | ASTM D 5308 |
| Viscoelastic properties, | DIN 53 513, |
| 0 and 60° C., 16 Hz, 50 N initial force and 25 N amplitude force | ISO 2856 |

TABLE 3-continued

| Physical tests | Standard/ Conditions |
|---|---|
| Complex Modulus E*, | |
| Loss factor tan δ | |
| Goodrich Flexometer test, | DIN 53 533 |
| 0.25 inch, 25 min, 23° C. start | ASTM D 623-A |
| Contact temperature | |
| Center temperature | |
| Permanent set | |
| DIN-abrasion, 10 N force | DIN 53 516 |
| Dispersion | ISO/DIN 11345 |

Examples 2 to 5

Examples 2 to 5 were carried out in accordance with the "general methods used". Examples 2 to 4 are comparative examples from the prior art. Example 5 is an inventive example.

The following quantities were used: 6.40 phr Si 69 and 1.5 phr sulfur were used in Example 2, 6.32 phr Si 264 and 2.2 phr sulfur were used in Example 3; and 5.75 phr Dynasilan 3201 and 2.2 phr sulfur were used in Example 4: 6.47 phr of the organosilicon compound according to the invention from Example 1 and 2.2 phr sulfur were used in Example 5. This corresponds to equimolar addition with a sulfur content adjusted in accordance with one of the silanes.

Table 4 gives the rubber engineering data for the crude mixture and the vulcanizate.

TABLE 4

| Feature | Units | Ex. 2 | Ex. 3 | Ex. 4 | Ex 5 |
|---|---|---|---|---|---|
| Crude mixture results | | | | | |
| ML (1 + 4) at 100° C. | [ME] | 58 | 57 | 63 | 63 |
| Dmax-Dmin | [dNm] | 16.5 | 16.0 | 10.6 | 10.7 |
| t 10% | [min] | 1.8 | 1.1 | 0.5 | 0.5 |
| t 90% | [min] | 26.8 | 25.1 | 26.2 | 27.4 |
| t 80%-t 20% | [min] | 10.2 | 8.2 | 9.9 | 10.4 |
| Vulcanization time | [min] | 50 | 50 | 40 | 50 |
| Vulcanizate results | | | | | |
| Tensile strength | [MPa] | 14.4 | 13.7 | 13.4 | 13.0 |
| Modulus 100% | [MPa] | 1.6 | 1.8 | 1.6 | 1.5 |
| Modulus 300% | [MPa] | 8.2 | 10.0 | 9.3 | 9.5 |
| Modulus 300/100% | [–] | 5.2 | 5.4 | 5.8 | 6.4 |
| Extension at break | [%] | 420 | 360 | 360 | 350 |
| Fracture energy | [J] | 81.3 | 64.6 | 58.0 | 52.7 |
| Shore-A hardness | [SH] | 63 | 63 | 55 | 55 |
| Ball rebound (23° C.) | [%] | 32.9 | 34.1 | 38.3 | 36.5 |
| DIN-abrasion | [mm³] | 89 | 75 | 58 | 65 |
| Dyn. exp. modulus E* (0° C.) | [MPa] | 19.9 | 20.5 | 12.7 | 14.8 |
| Dyn. exp. modulus E* (60° C.) | [MPa] | 8.3 | 8.8 | 6.2 | 7.1 |
| Loss factor tan δ (0° C.) | [–] | 0.505 | 0.482 | 0.454 | 0.473 |
| Loss factor tan δ (60° C.) | [–] | 0.114 | 0.104 | 0.099 | 0.090 |
| Contact temperature | [° C.] | 67 | 68 | 62 | 61 |
| Insertion temperature | [° C.] | 118 | 118 | 113 | 112 |
| Permanent set | [%] | 5.0 | 3.8 | 3.3 | 2.8 |
| Dispersion Phillips | [–] | 8 | 9 | 7 | 9 |

The mixture from Example 5 with the organosilicon compound according to the invention from Example 1 shows, as compared with the reference mixtures, a very good set of static properties. In particular, the 300%/100% modulus reinforcement factor is significantly higher than the reference mixtures, which indicates a high yield of filler-rubber bonds. In addition, the loss factor tan δ(60° C.), which correlates with the rolling resistance, is advantageously low. Furthermore, the build-up of heat by the mixture in the Goodrich Flexometer test is lowest for the mixture from Example 5.

In addition, the advantageous, high, thermal stability of the silane according to the invention is very obvious. Thus, there is hardly any increase in torque detected in the unaccelerated mixture at 165° C (FIG. 1). This shows that the unaccelerated mixture with the silane according to the invention is much less sensitive to scorching during the mixing process than, for example, Si 69.

What is claimed is:

1. An organosilicon compound of general formula (I)

$$R^1R^2R^3Si-R^4-S-Zn-S-R^4-SiR^1R^2R^3 \quad (I)$$

wherein

R$^1$, R$^2$, R$^3$, independently, represent H, a halogen, a straight-chain or branched alkyl group or a straight-chain or branched alkoxy group and R$^4$ represents a straight-chain or branched alkylidene group.

2. Organosilicon compounds according to claim 1, wherein R$^1$, R$^2$, R$^3$=ethoxy and R$^4$=CH$_2$CH$_2$CH$_2$ or isobutylidene.

3. A process for preparing organosilicon compounds according to claim 1, comprising:

reacting a mercaptan compound of general formula (II)

$$R^1R^2R^3Si-R^4-S-H \quad (II),$$

wherein

R$^1$, R$^2$, R$^3$, independently, represent H, a halogen, a straight-chain or branched alkyl group or a straight-chain or branched alkoxy group and R$^4$ represents a straight-chain or branched alkylidene group, with zinc alcoholate.

4. A process for preparing organosilicon compounds according to claim 3, comprising carrying out the reaction at a temperature range of 20° to 200° C.

5. A process for preparing organosilicon compounds according to claim 3, comprising carrying out the reaction in an alcoholic solution.

6. A process for preparing organosilicon compounds according to claim 3, comprising reacting a compound of formula (II) in which R$^1$, R$^2$, R$^3$=ethoxy and R$^4$=CH$_2$CH$_2$CH$_2$, with zinc ethanolate in ethanolic solution.

7. A method for using the organosilicon compound according to claim 1 in rubber mixtures, comprising:

incorporating the organosilicon compound according to claim 1 in a mixture comprising rubber and filler.

8. Rubber mixtures, comprising rubber, filler and at least one organosilicon compound of formula (I).

9. Rubber mixtures according to claim 8, wherein the at least one organosilicon compound of formula (I) is used in an amount of 0.1 to 15 wt. %, with respect to the amount of filler used.

10. Rubber mixtures according to claim 8, comprising synthetic rubber and silica as filler.

11. A process for preparing rubber mixtures according to claim 8, comprising mixing rubber, filler and at least one organosilicon compound of formula (I).

12. Molded items, prepared from the rubber mixtures in accordance with claim 8.

* * * * *